(12) United States Patent
Franco

(10) Patent No.: US 11,141,302 B1
(45) Date of Patent: Oct. 12, 2021

(54) WATER SHOE WITH BRACE

(71) Applicant: ABLE Footwear, LLC, Cypress, TX (US)

(72) Inventor: Brittany Franco, Cypress, TX (US)

(*) Notice: Subject to any disclaimer, the term of this patent is extended or adjusted under 35 U.S.C. 154(b) by 0 days.

(21) Appl. No.: 16/297,344

(22) Filed: Mar. 8, 2019

Related U.S. Application Data (60) Provisional application No. 62/640,038, filed on Mar. 8, 2018.

(51) Int. Cl.
| | |
|---|---|
| A43B 5/08 | (2006.01) |
| A61F 5/01 | (2006.01) |
| A63B 31/11 | (2006.01) |
| A43B 7/22 | (2006.01) |
| A43B 7/20 | (2006.01) |

(52) U.S. Cl.
CPC .............. *A61F 5/0111* (2013.01); *A43B 5/08* (2013.01); *A43B 7/20* (2013.01); *A43B 7/223* (2013.01); *A63B 31/11* (2013.01)

(58) Field of Classification Search
CPC ..... A61F 5/0111; A61F 5/0113; A61F 5/0116; A61F 5/0127; A43B 7/20; A43B 7/22; A43B 7/223; A43B 5/08
USPC .......................................................... 36/109
See application file for complete search history.

(56) References Cited

U.S. PATENT DOCUMENTS

| | | | | |
|---|---|---|---|---|
| 1,332,047 A | * | 2/1920 | Lasher | A61F 5/0113 602/27 |
| 1,336,001 A | * | 4/1920 | Tranmer | A61F 5/0127 602/27 |
| 2,663,294 A | * | 12/1953 | Harrison | A61F 5/0113 602/28 |
| 3,827,430 A | * | 8/1974 | Fadden | A61F 5/0113 602/28 |
| 5,771,610 A | * | 6/1998 | McDonald | A43B 5/08 36/116 |
| 6,302,858 B1 | * | 10/2001 | DeToro | A61F 5/0111 602/23 |
| 2012/0255194 A1 | * | 10/2012 | Schwartz | A61F 5/0127 36/19.5 |
| 2013/0036628 A1 | * | 2/2013 | Hussey | A43B 3/0078 36/87 |
| 2016/0206037 A1 | * | 7/2016 | McCormick | A43B 5/08 |
| 2016/0286896 A1 | * | 10/2016 | Biancucci | A43B 13/223 |
| 2018/0242685 A1 | * | 8/2018 | Jackinsky | B32B 3/263 |

* cited by examiner

*Primary Examiner* — Ted Kavanaugh
(74) *Attorney, Agent, or Firm* — Karen B. Tripp (57) ABSTRACT

A water or swim shoe for persons needing to wear an orthotic to support a foot for swimming or any other water exercise or recreation. The shoe body is comprised of porous, water resistant material, has multiple holes for water drainage, and a protective rounded rubber toe end. The shoe sole is comprised of rubber or synthetic rubber. The shoe sole has affixed thereto and extending from the heel end an "L" shaped hard plastic orthotic which is strapped to the back of the person's leg for wear.

16 Claims, 16 Drawing Sheets

WATER SHOE WITH BRACE

CROSS REFERENCE TO RELATED APPLICATION

The invention claims priority from U.S. Provisional Patent Application No. 62/640,038, filed Mar. 8, 2018.

STATEMENT REGARDING FEDERALLY SPONSORED RESEARCH OR DEVELOPMENT

This invention is not the result of federally sponsored research.

REFERENCE TO SEQUENCE LISTING, A TABLE, OR A COMPUTER PROGRAM LISTING, OR A COMPACT DISK APPENDIX

None

BACKGROUND

1. Field of the Invention

The present invention relates to water or swim shoes and to braces for feet.

2. Description of Relevant Art

Enjoyment of water sports, even as simple as water slides and swimming, is problematic for children and adults who must wear braces on their feet. Braces, by their nature, are typically comprised of materials that should remain dry, and drying wet braces is time consuming and sometimes tedious.

Brace manufacturers typically advise against swimming in the ocean, lakes or swimming pools, or even taking a shower, while wearing braces or supports and orthoses in general. Soft braces can absorb water, which makes them heavy, so they can slip and no longer remain in the proper location. Salt water particularly can attack the materials in the supports and orthoses and impair both the efficacy and the comfort in wear of the medical device.

Nevertheless, from a therapeutic point of view, and even for enjoyment of water activities, it can be necessary to wear a brace in water. A need exists for ways a person can wear braces in water without concern about damaging the braces with the water and without having the time consuming task of drying the braces afterwards. A need exists for a supportive and protective water shoe that enables the wearer to have needed support and protection in water that would be usually be afforded by a brace without the wearer having to wear their usual brace in the water.

SUMMARY OF THE INVENTION

The present invention meets these needs with a water or swim shoe that provides an ankle and foot orthotic to support a foot for swimming or any other water exercise or recreation. The orthotic has a general "L" shape comprising a lower horizontal portion and an upper vertical portion and is comprised of a hard, rigid material resistant to or effectively unchanged by water (or salt water), such as, for example, hard plastic or a polymeric material, or aluminum or an aluminum alloy not including any iron) and sufficiently strong to serve its purpose as an orthotic.

The horizontal portion of the orthotic is tucked inside the heel end of the shoe and lies in a trench within the sole. The vertical portion of the orthotic extends from the heel end upward adjacent the leg of the wearer. These horizontal and vertical portions join in an obtuse curved angle to form the corner of the general "L" shaped orthotic behind the heel end of the shoe. One or more straps, preferably with padding or pads, hold the orthotic to the leg with elastic or a fastener or securer comprised of, for example, a hook and loop closure, snaps, or ties. Similarly, one or more straps on the shoe body allow for adjustment of the fit of the shoe on the foot.

The body of the shoe is comprised of a porous or mesh type water resistant, non-absorbent, or quick-drying material and has one or more larger holes for water drainage. The sole of the shoe is comprised of rubber or synthetic rubber or a similar water resistant vinyl, and in one embodiment can extend over the top of the toe end of the shoe for protection of the toes. The body of the shoe also has a support, preferably with padding, in the area of the person's ankle. In one embodiment, the shoe appears somewhat like a sandal, with no covering extending up the leg. In another embodiment, the shoe body has comprises more material, more like a sneaker. In still another embodiment, the shoe has a sleeve that extends at least partially up the leg to help hold the orthotic in place. Such sleeve is comprised of neoprene or other water-resistant material and can be porous.

DETAILED DESCRIPTION OF THE INVENTION

The present invention provides and all in one, supportive shoe, for use in and around water. In one embodiment, the shoe has interchangeable levels of support. In the embodiments, shown in the Figures, the water or swim shoe 10 of the invention has a built in orthotic device 12 to support the wearer's ankle and lower leg and provide stability for persons with weak lower limbs, foot drop, or other diagnosis' which require orthotic devices.

Figure 14:
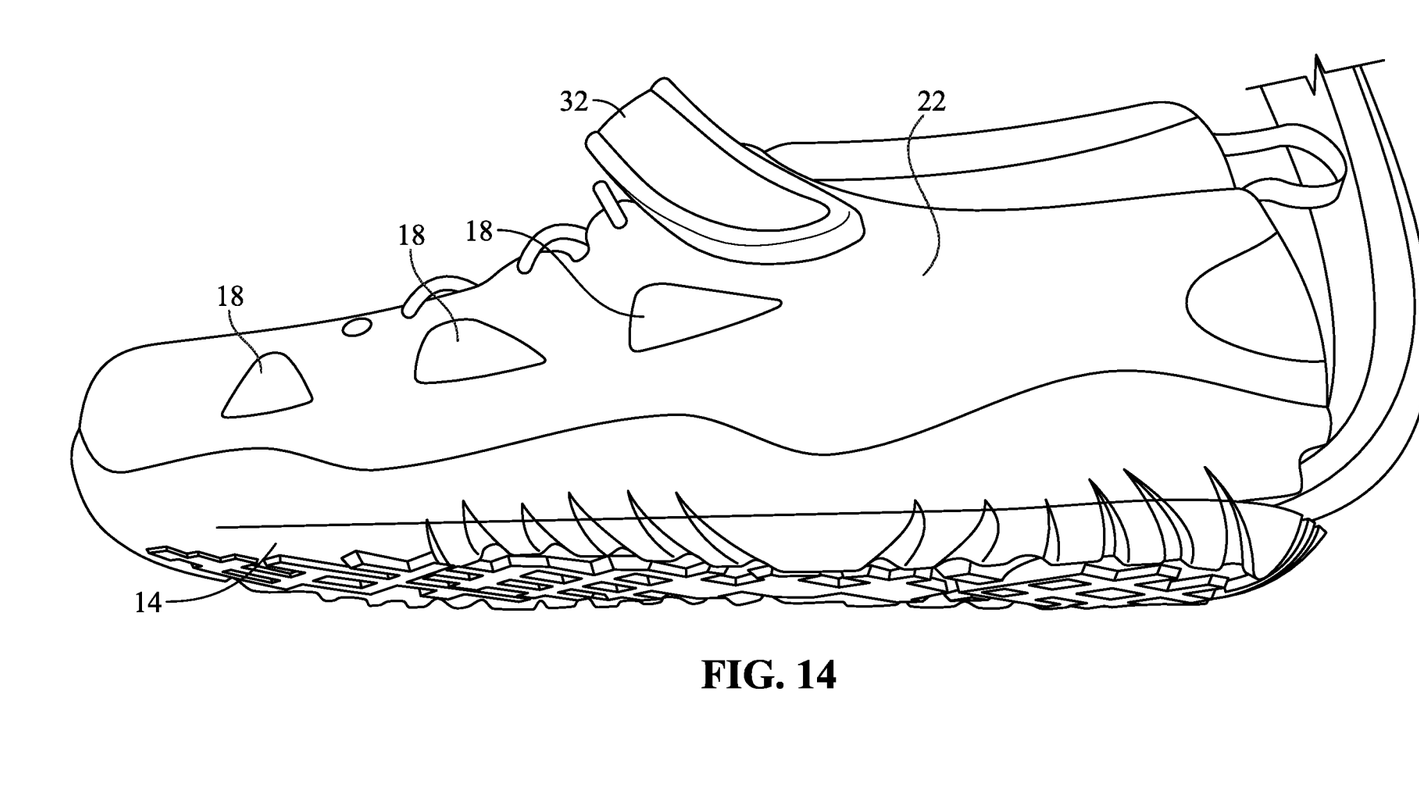
FIG. 14 is a side bottom perspective view of the shoe of FIGS. 9 and 11 showing the orthotic inserted in the sole of the shoe and extending upward from the sole.
Figure 15:
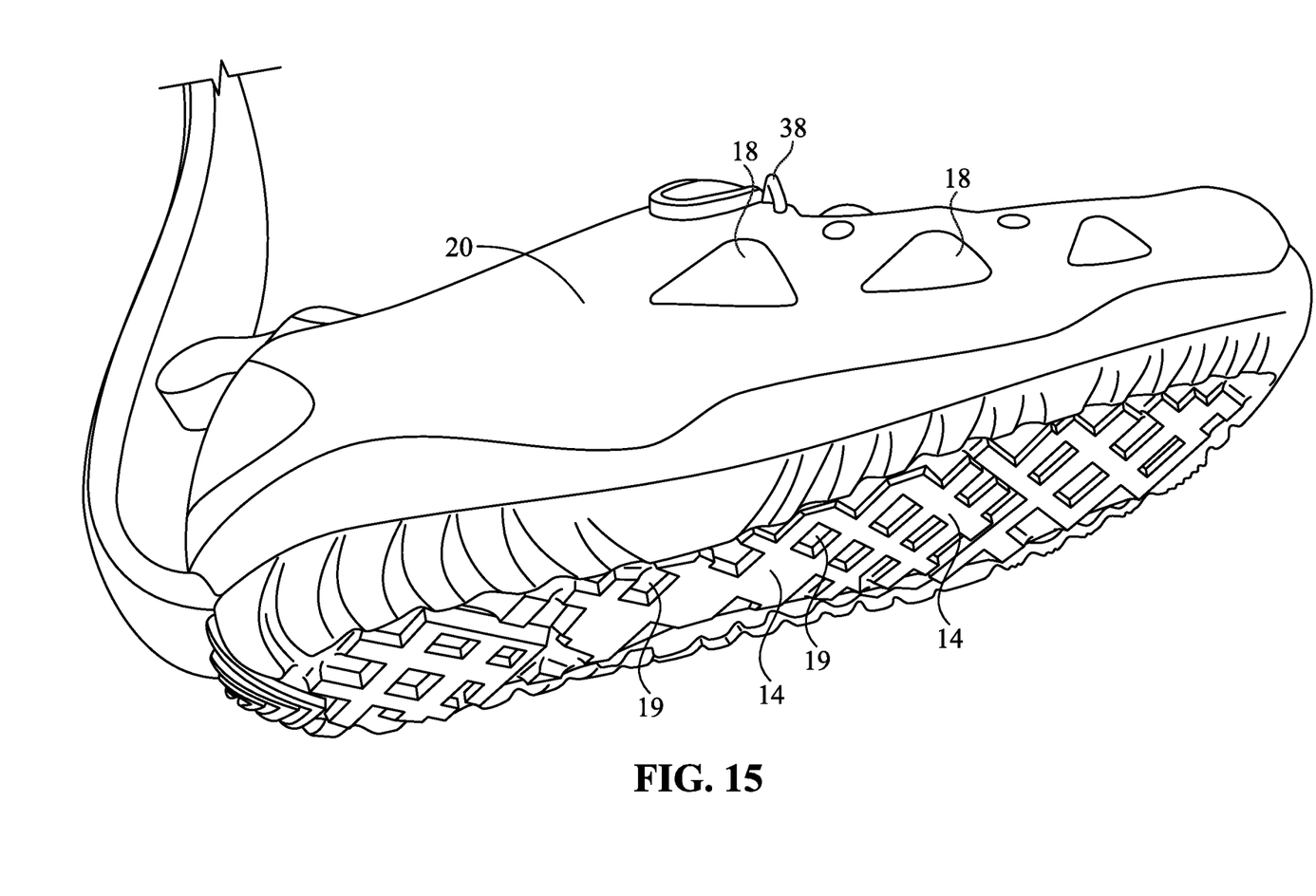
FIG. 15 is a bottom perspective view of the shoe of FIG. 9 showing the tread on the shoe for improving grip and reducing slippage for the wearer of the shoe.
Figure 16:
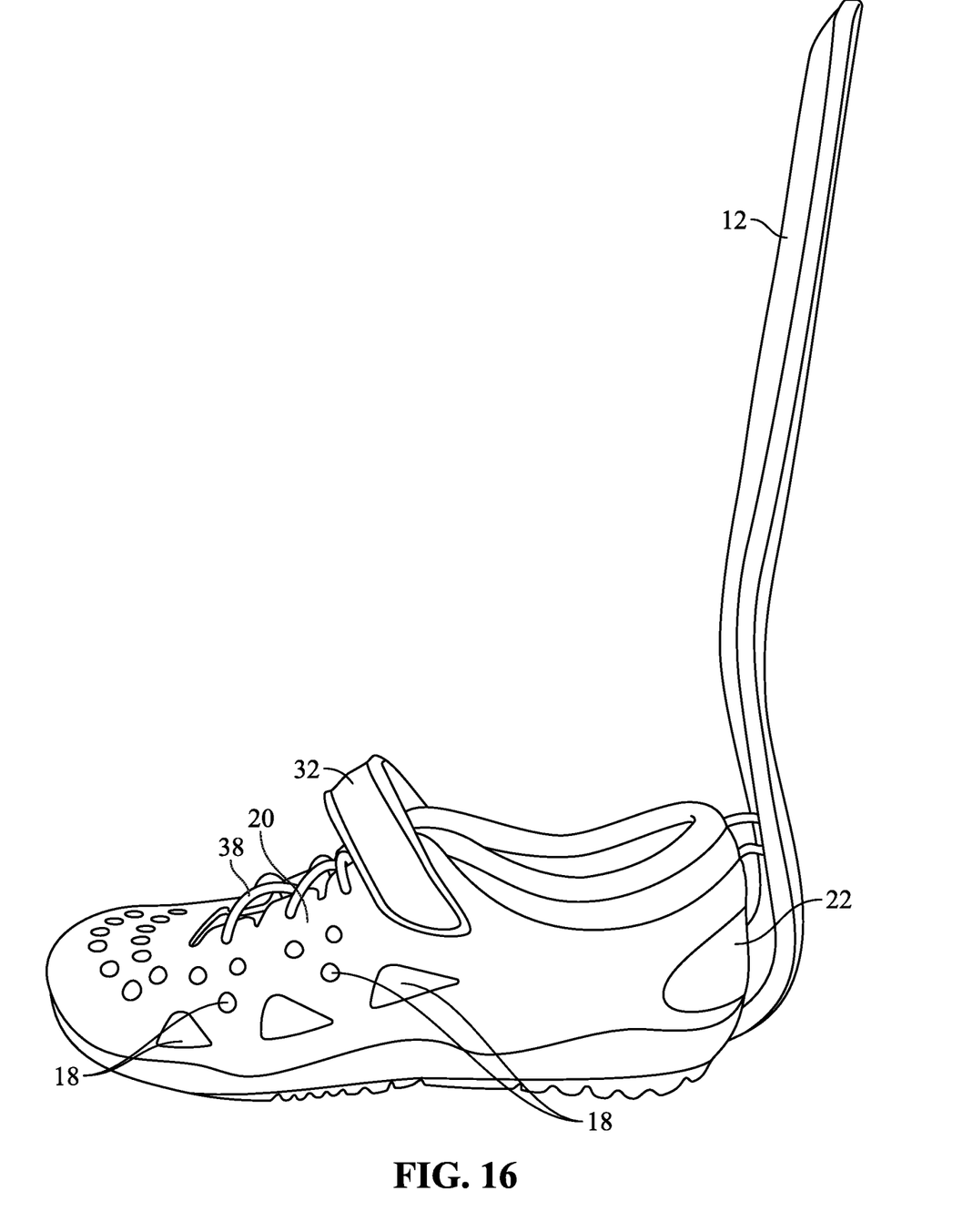
FIG. 16 is a side perspective view of the shoe of FIG. 9 without the padding and strap on the orthotic.
Figure 17:
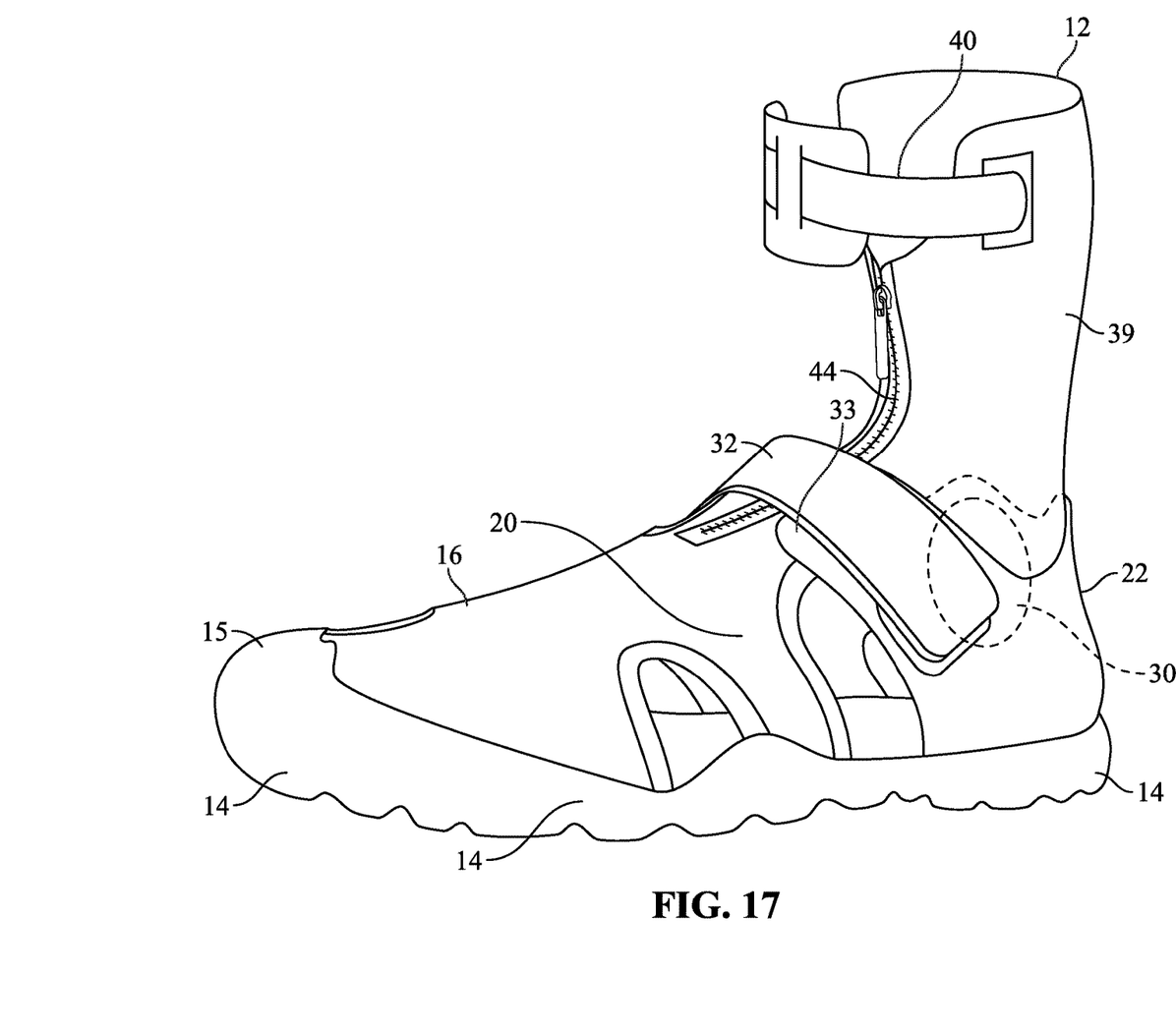
FIG. 17 is a side perspective view of a third alternative embodiment of the shoe of the invention, showing the orthotic held in place at least partially with a sleeve and a strap.

In the embodiments shown in FIGS. 1-16, the shoe of the invention has a rubber, preferably perforated, (natural or synthetic) sole 14, and a perforated, removable foot bed (not shown), to allow for water drainage. Alternative materials having similar properties as rubber for this purpose—that is, for use of the shoe in water—could alternatively be used, and the term "rubber" as used herein shall be understood to include such materials. In one embodiment, the rubber sole 14 extends up over the toe 15 of the shoe, preferably in a rounded design, as shown in FIG. 17, to help protect the wearer's toes. In the embodiment shown in FIG. 17, the shoe 10 has a nylon (or similar water resistant) material or mesh fabric upper body 16 to allow for quick drying, although again alternative materials which could function for the same purpose, that is, use of the shoe in water, could be used and are intended to be included herein. The shoe 10 will also have openings 18, preferably decorative openings, along the sides 20 to allow for drainage and debris (such as sand, etc) to easily exit the shoe, as shown for example in FIGS. 1-17. The sole 14 has an outer surface with a pattern of relief or treads 19 for gripping a wet walking surface and avoiding slippage by the wearer, as shown in FIGS. 14 and 15.

The hard orthotic 12, similar in the embodiments shown in FIGS. 1-16 to a posterior leaf spring ankle foot orthotic, positioned at the rear 22 of the shoe 10, is comprised of material(s) that is not corroded or substantively or effectively changed by water or salt water, such as hard plastic or similar synthetic polymeric material, or a metal that is light in weight and not corroded by water or sea water, such as for example, an aluminum alloy that does not include any iron, or stainless steel, that resists water, or does not absorb water, and is sufficiently strong and light in weight to serve its purpose of acting as a brace or support for the foot and ankle of the wearer, that is, its purpose as an orthotic.

Figure 1:
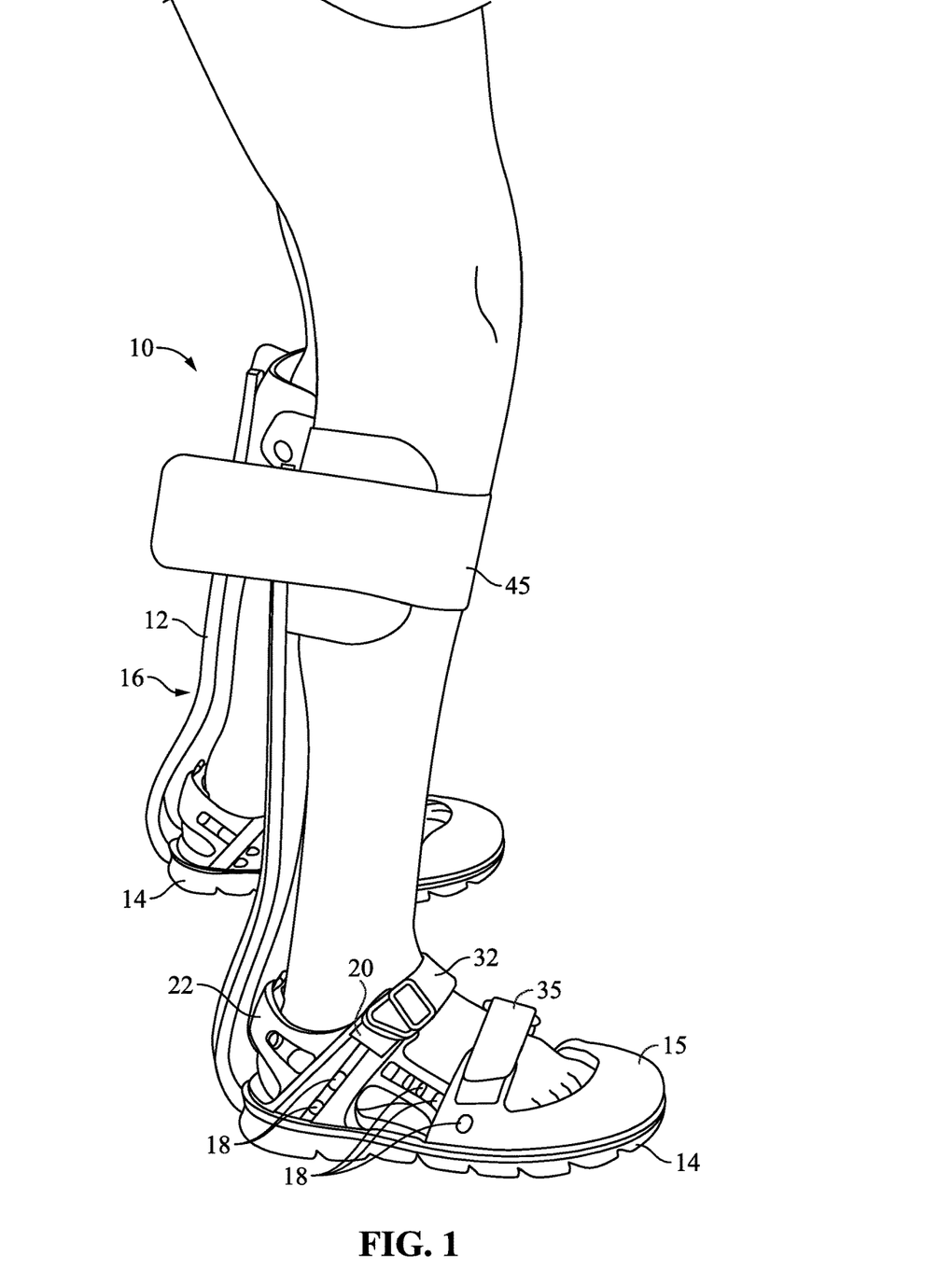
FIG. 1 is a side perspective view of one embodiment of the invention as shown worn on a child's leg.
Figure 2:
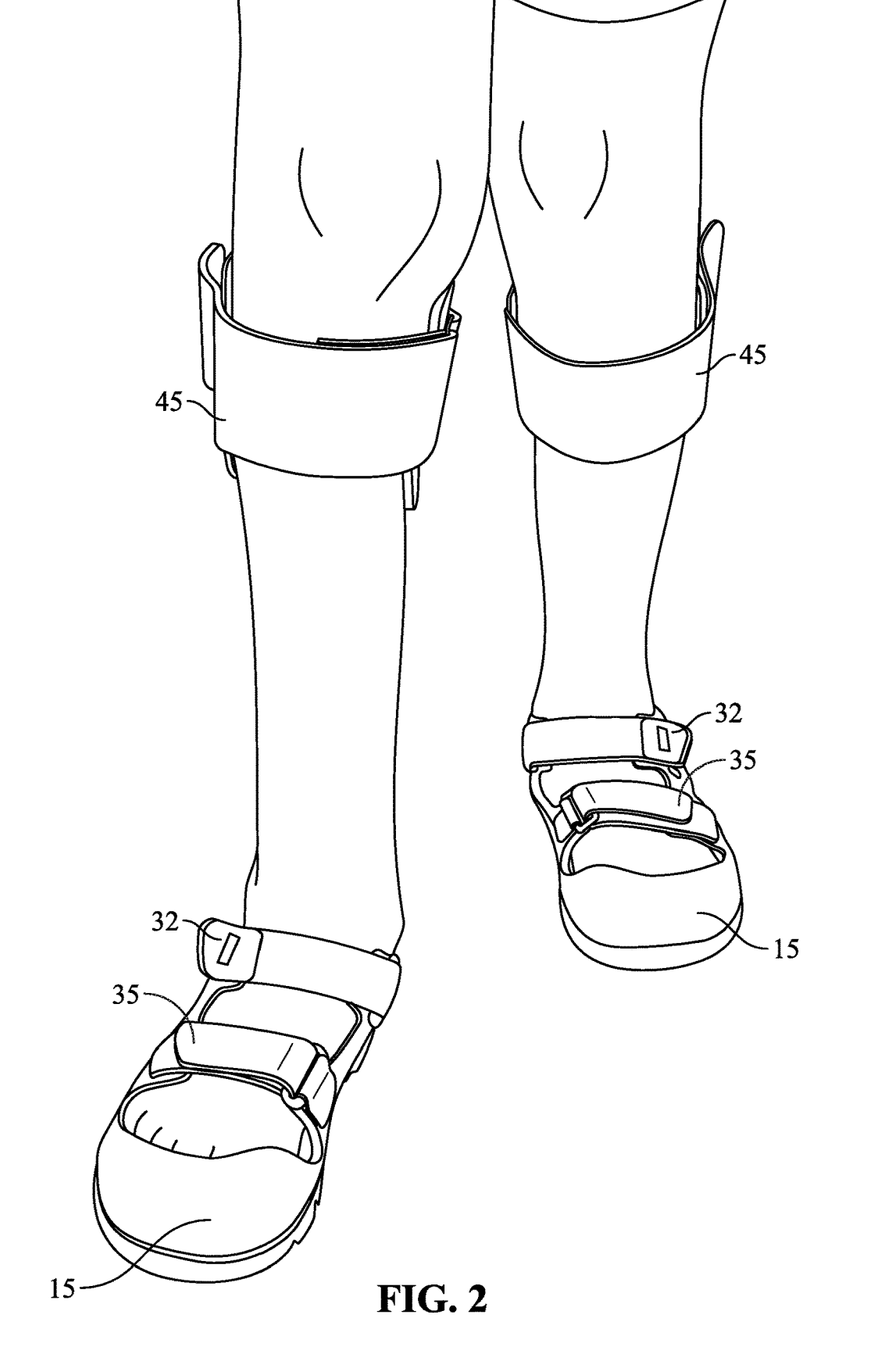
FIG. 2 is a front perspective view of the embodiment of the invention of FIG. 1, as shown worn on a child's leg.
Figure 3:
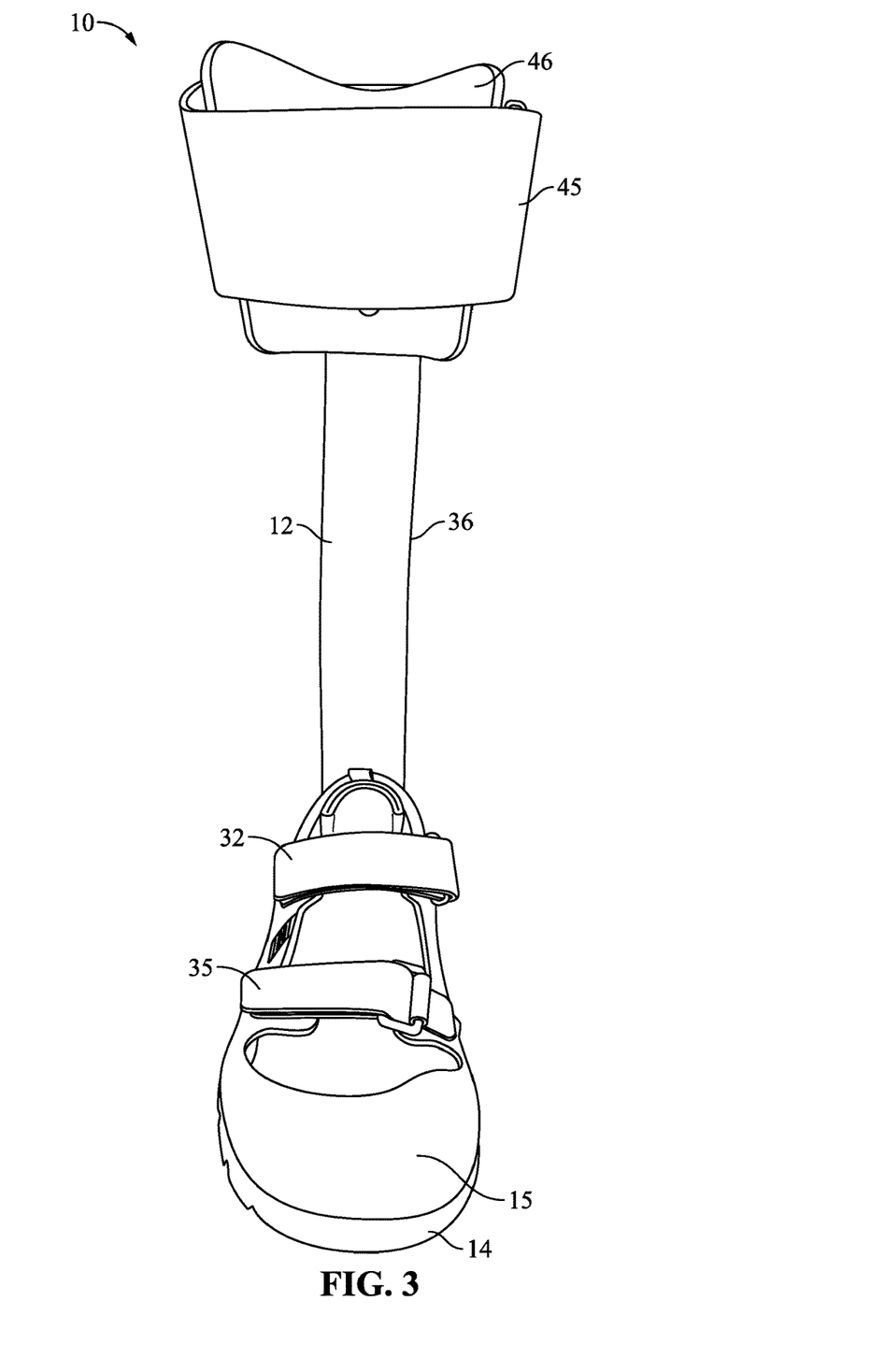
FIG. 3 is a front view of the embodiment of the invention of FIG. 1.
Figure 4:
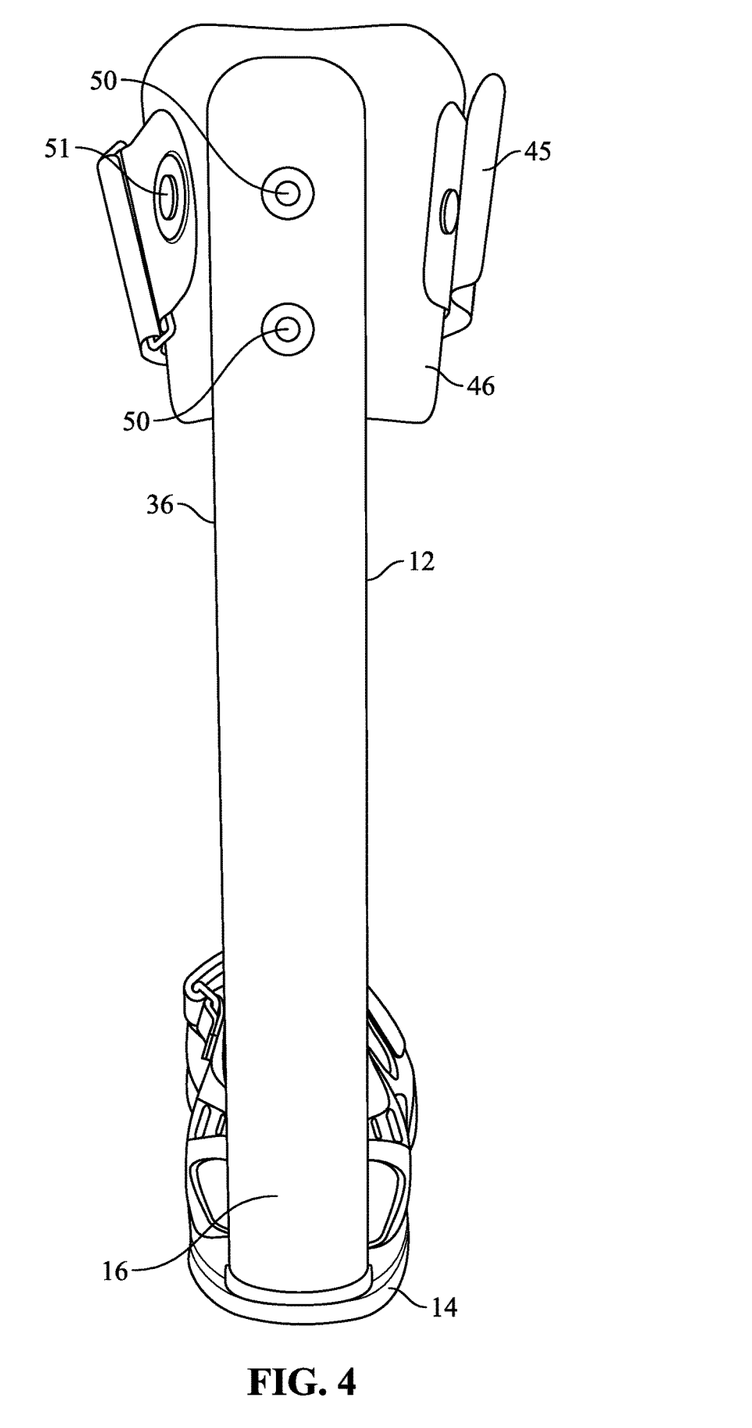
FIG. 4 is a back view of the embodiment of the invention of FIG. 1.

In some embodiments not shown, the orthotic 12 is removable and interchangeable to allow for different levels of support. In such embodiment, the orthotic 12 is attachable to the shoe with attachers such as, for example, straps, clips, screws, or clamps, and the like, and the orthotic is positioned at least in part in the sole 14 of the shoe 10, just as shown in FIG. 4 for a shoe with a non-removable orthotic, for example.

Figure 11:
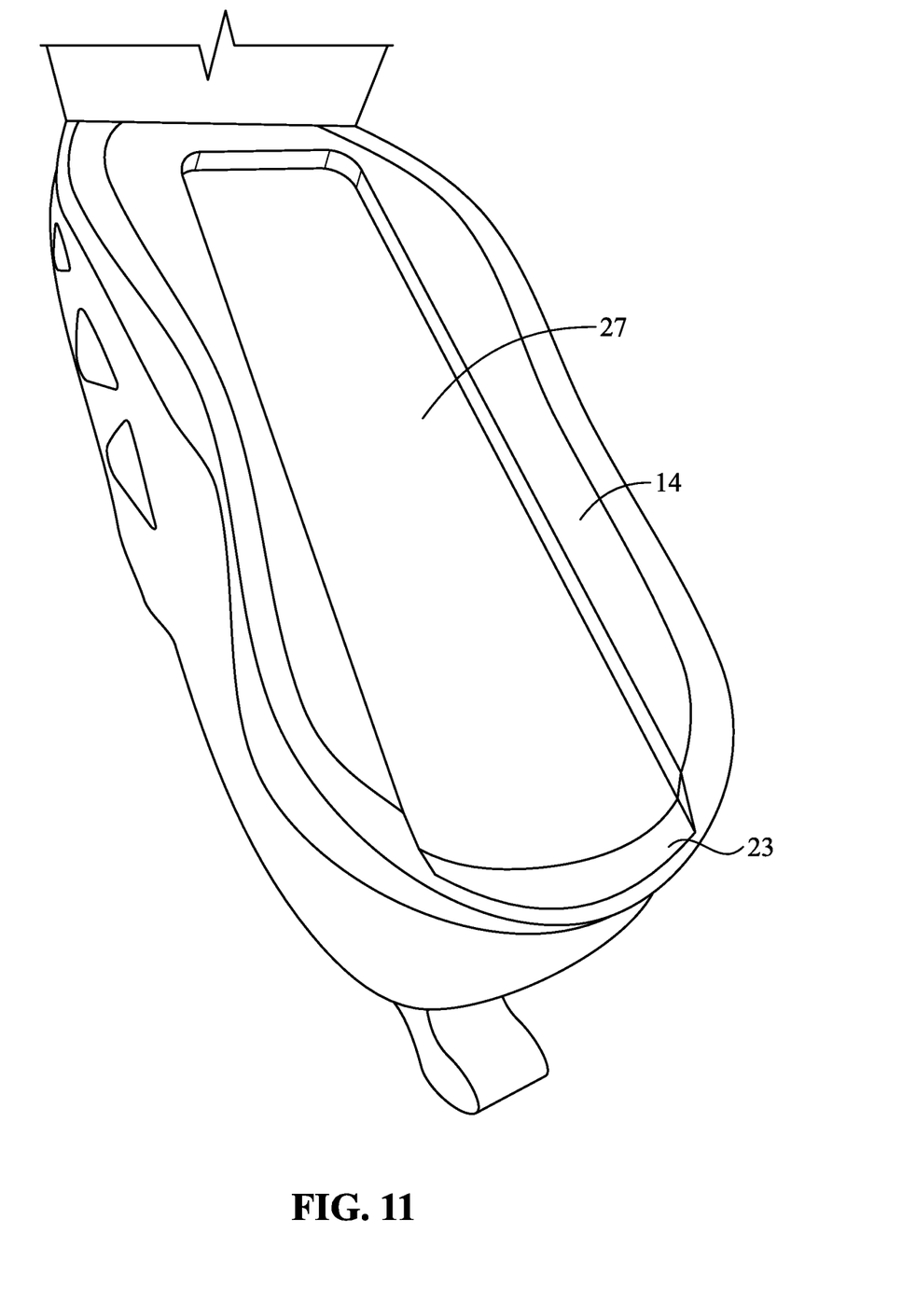
FIG. 11 is a bottom view of the shoe of the embodiment of FIG. 10 showing the trench for insertion of the orthotic.
Figure 12:
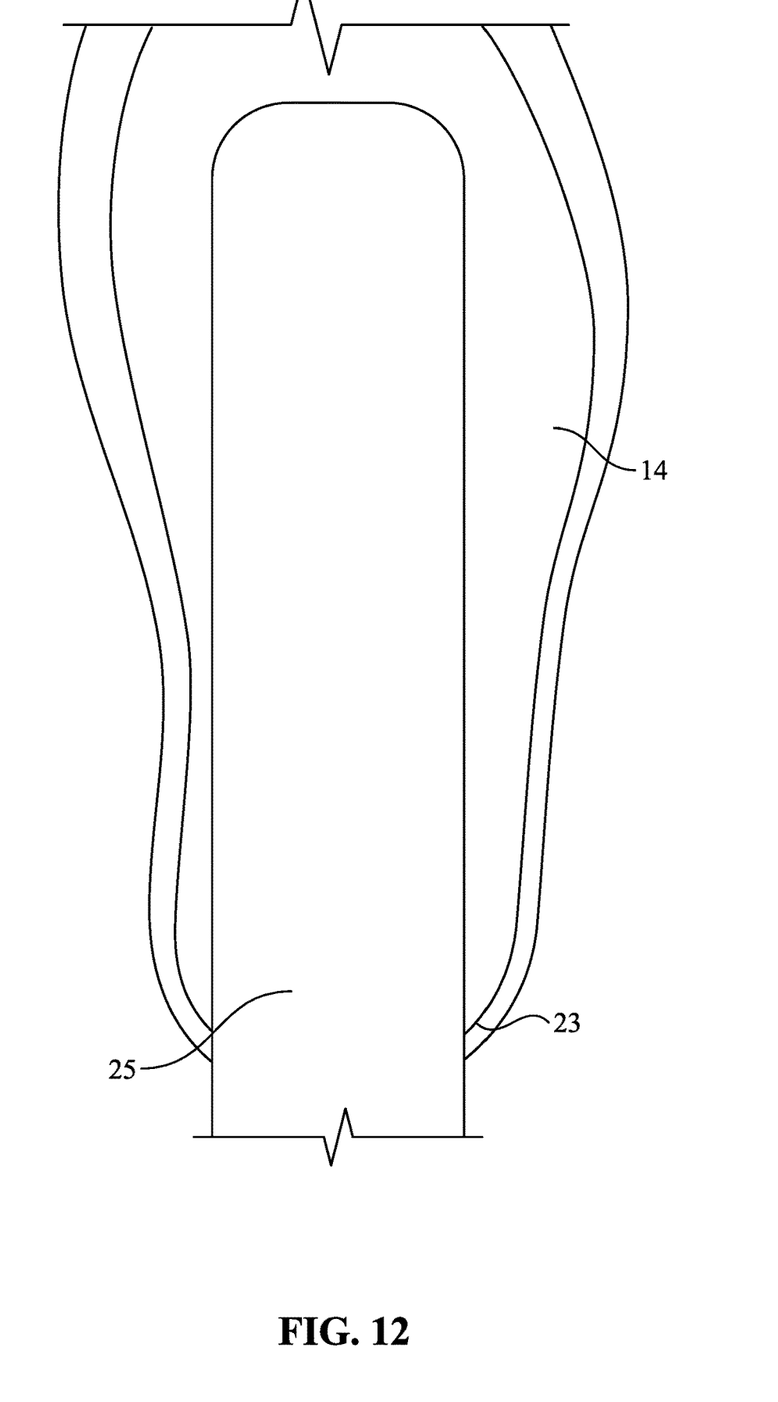
FIG. 12 is a bottom view of the shoe of the embodiment of FIGS. 10 and 11 showing the orthotic in the trench in the sole of the shoe.
Figure 13:
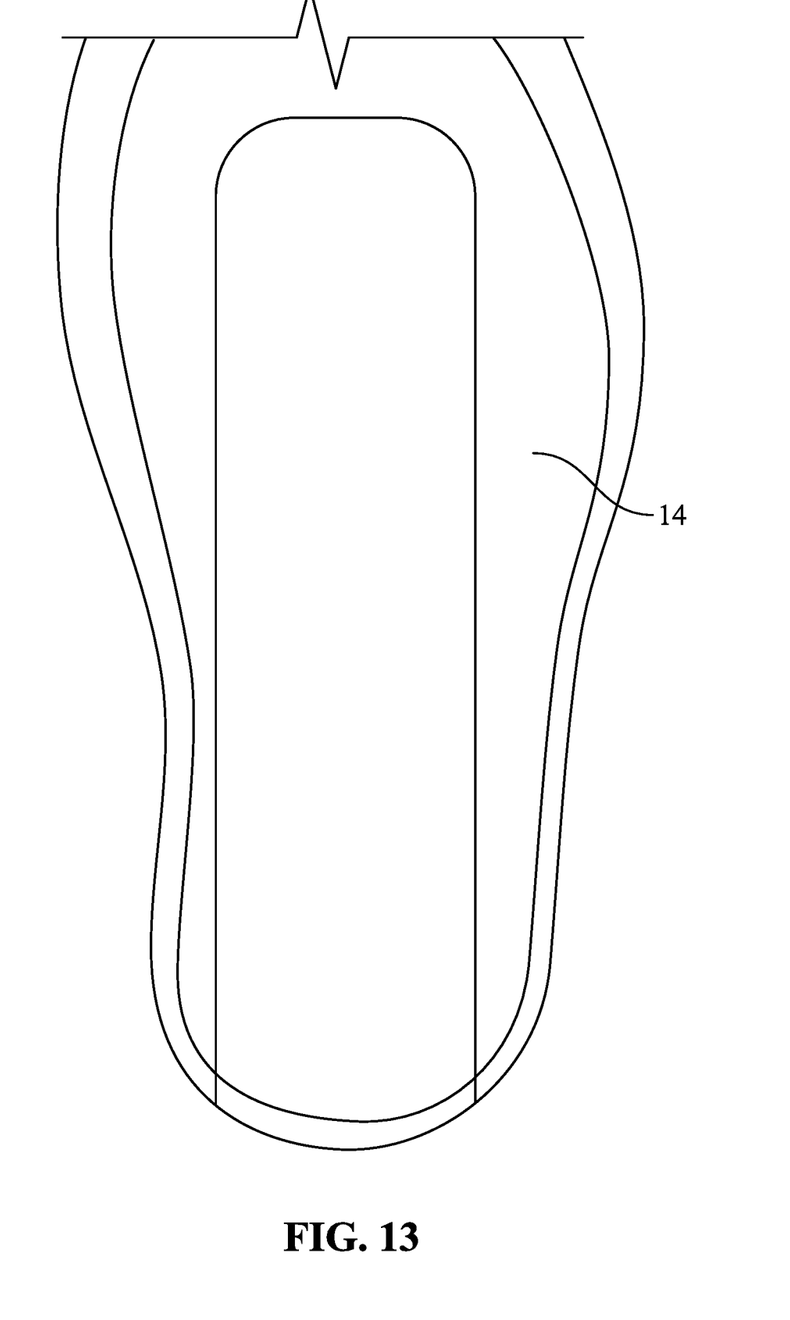
FIG. 13 is a bottom view of the shoe of the embodiment of FIG. 10 with the pulled away part of the sole put back into place.

In some other embodiments, the orthotic device 12 is permanently affixed to the shoe 10, as shown, for example, in FIGS. 1-17, with an affixer such as, for example, waterproof glue attaching the orthotic to the shoe sole. The horizontal portion 25 of the orthotic device 12, as shown in FIG. 12, is inserted in the heel end 23 of the sole 14 and positioned to lay in a trench 27 within the sole 14, as shown in FIGS. 11 and 12.

As shown in FIG. 1-7, the vertical portion 36 of the orthotic 12 is preferably comprised of one piece together with the horizontal portion 25 of the orthotic 12. That is, preferably the orthotic 12 is one piece.

Pad 46, as shown in FIGS. 1-7, is attached to the horizontal portion 36 of the orthotic 12 with fasteners or attachers 50 (such as, for example, screws, clips or brads). Strap 45 holds the orthotic in place on a wearer's leg and is attached to pad 50 with fasteners such as the brad or clip shown in FIGS. 4, 5, and 7 and the buckle frame 52 shoe in FIGS. 5 and 7.

Pad 46 is comprised of a material that prevents strap 45 from chafing the leg of the wearer, such as a foam material or shearling, and should be a material that maintains its function when wet, does not disintegrate in water, and preferably dries quickly. Pad 46 should have an exterior layer or backing that is capable of receiving the fasteners 50 for firmly holding the orthotic 12 to the pad 46 without tearing or stretching. One example is a soft plastic backing material.

Figure 5:
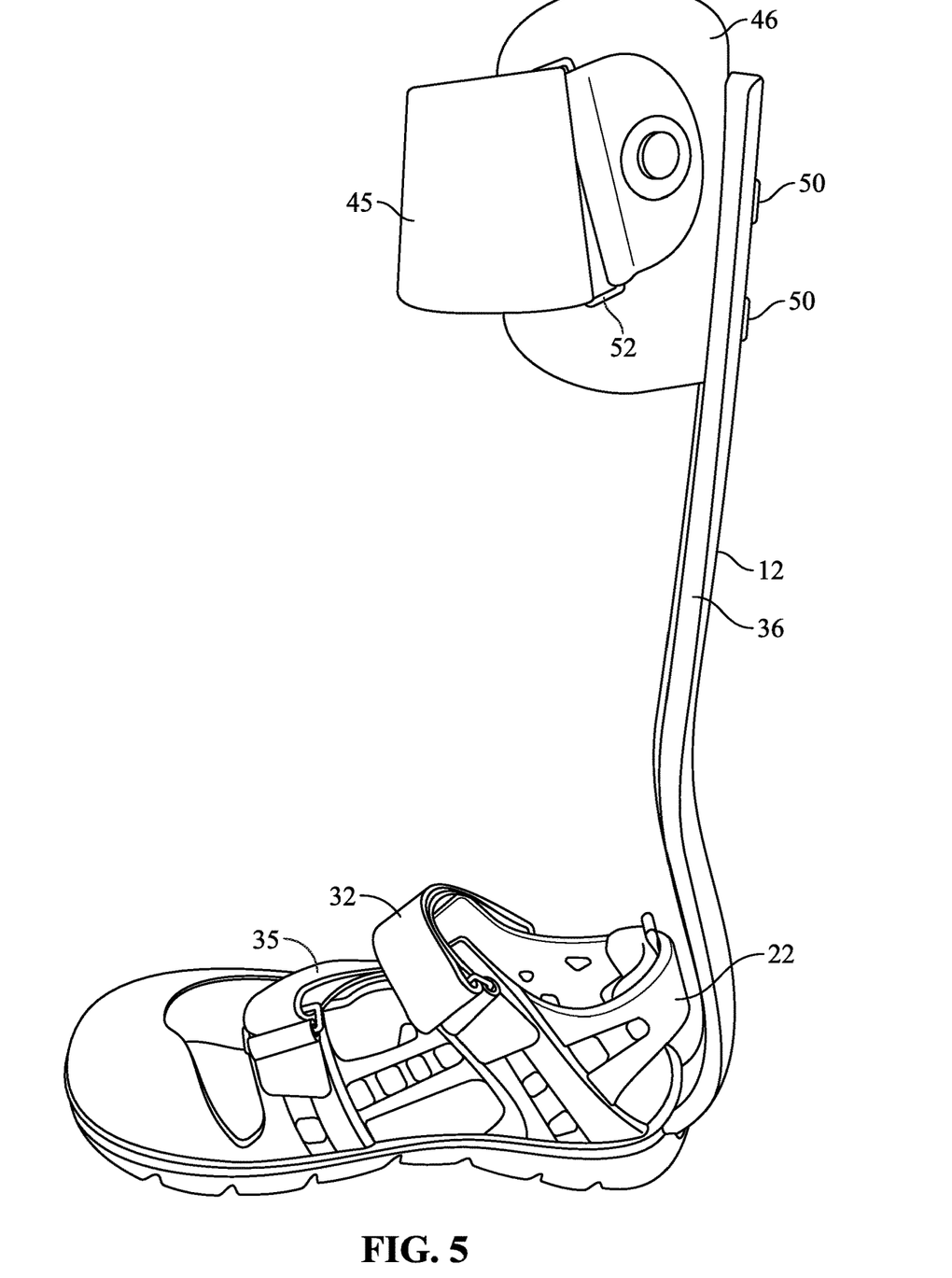
FIG. 5 is a top left side perspective view of the embodiment of FIG. 1.
Figure 6:
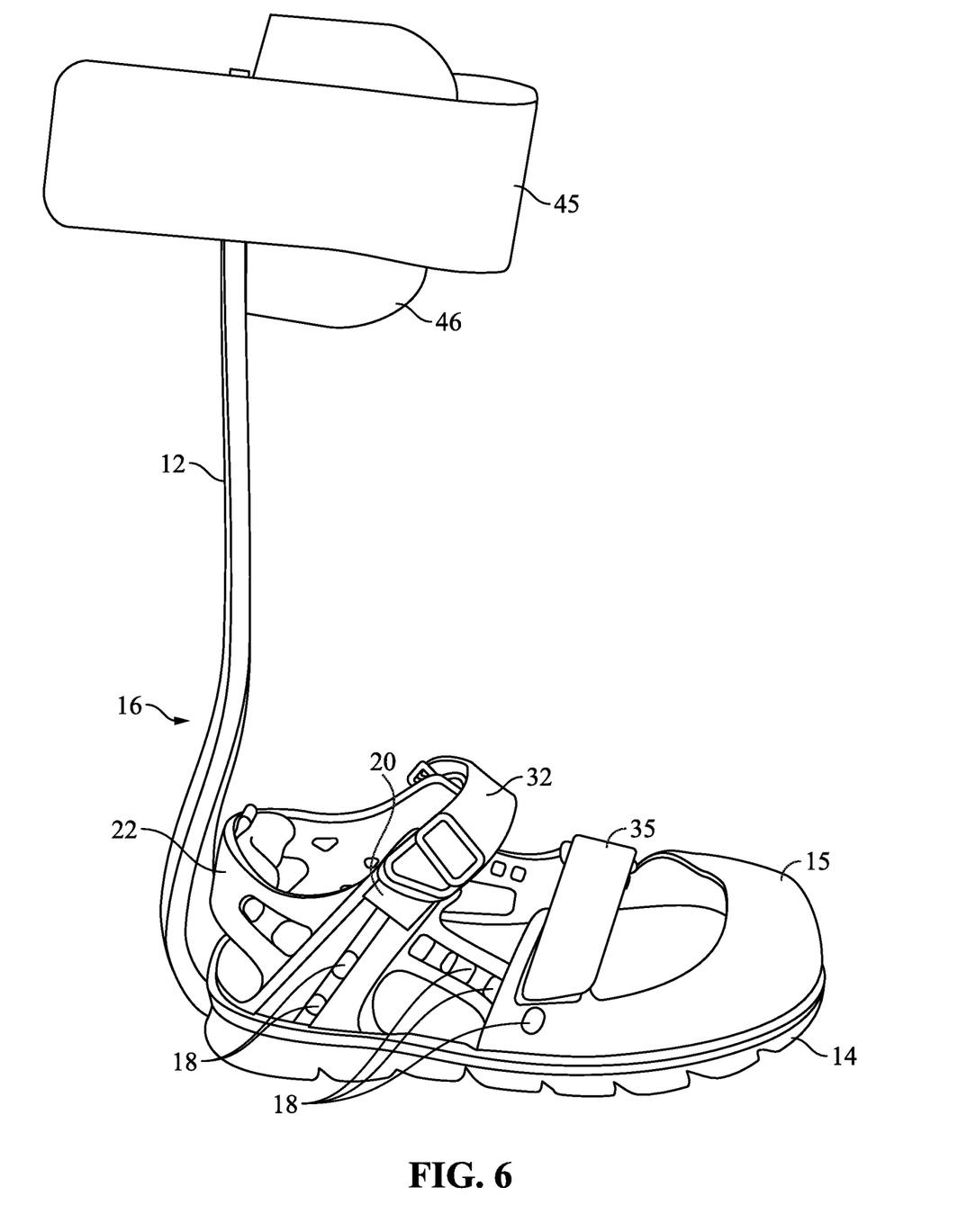
FIG. 6 is a top right side perspective view of the embodiment of FIG. 1.
Figure 7:
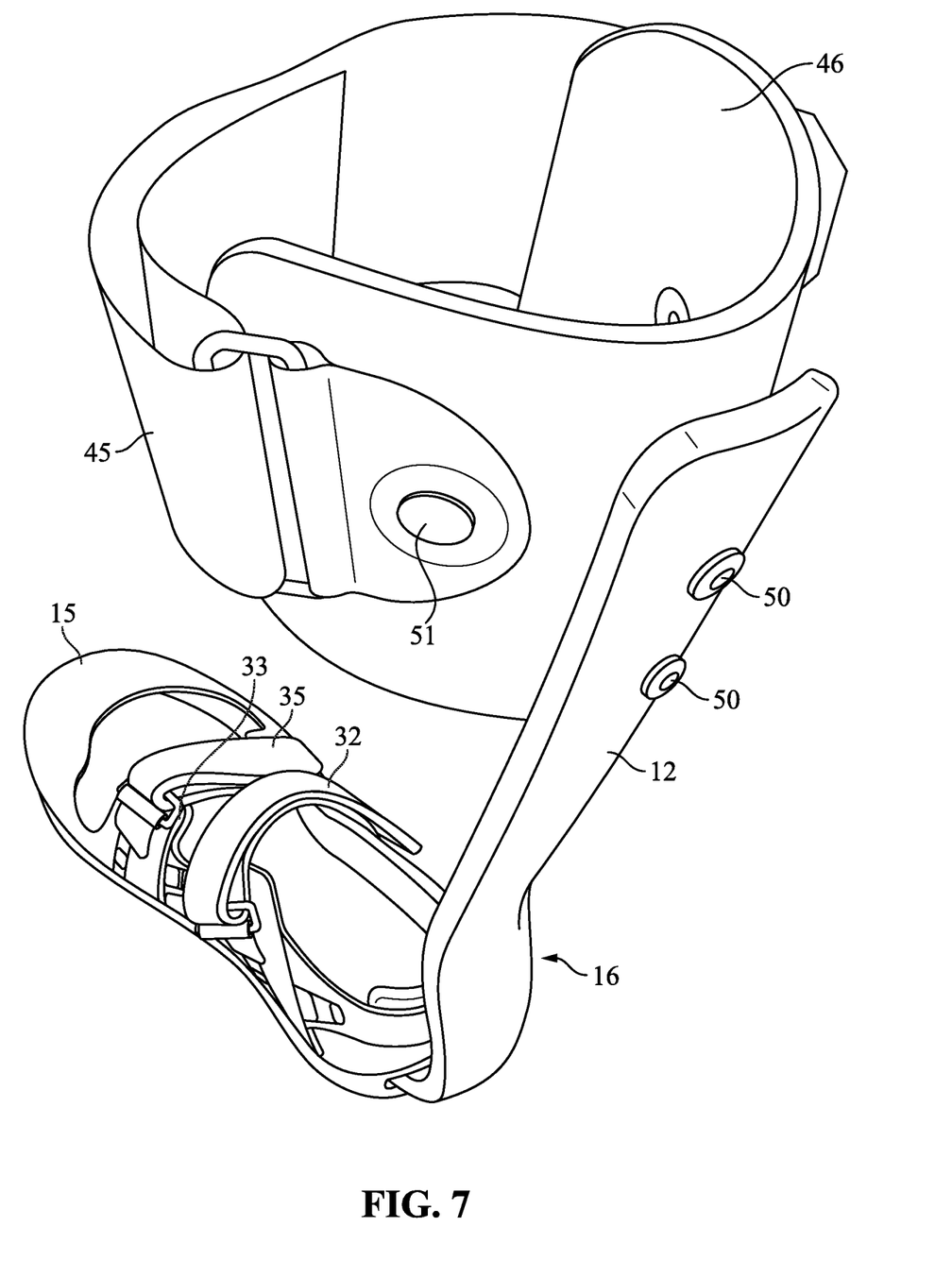
FIG. 7 is a top perspective view of the embodiment of FIG. 1.
Figure 8:
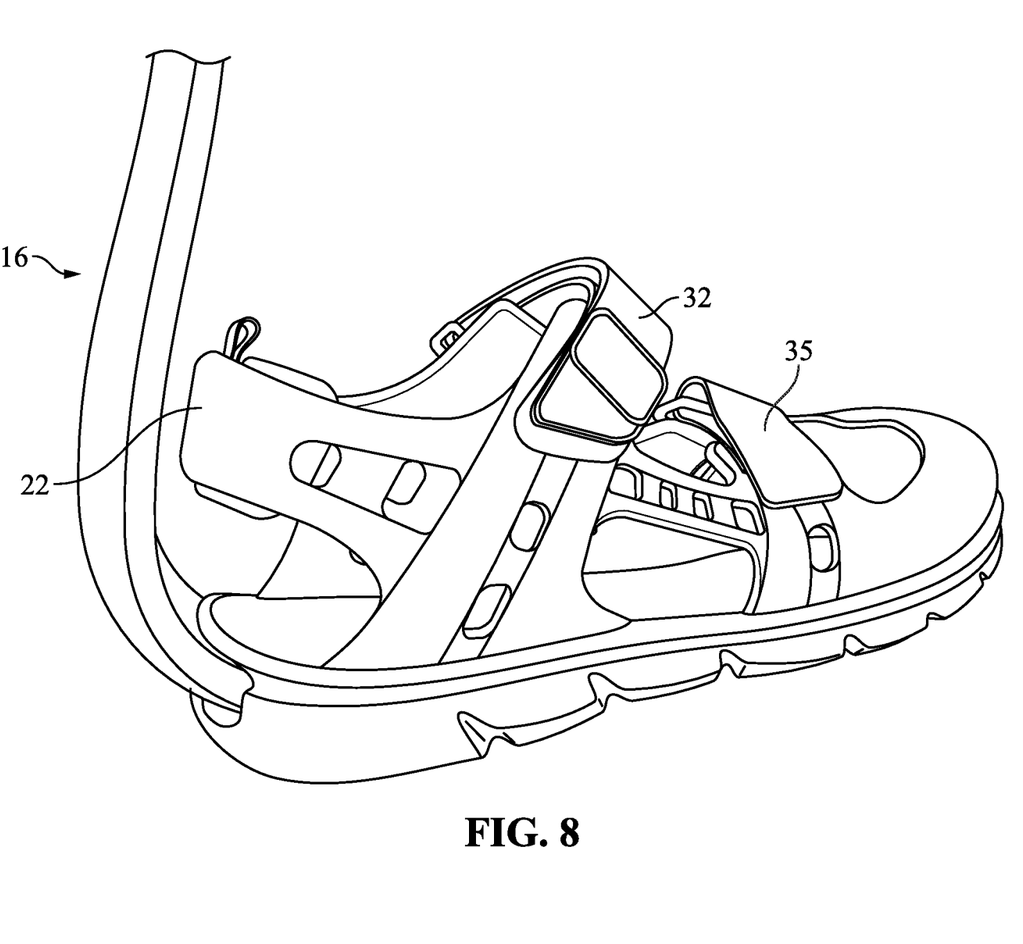
FIG. 8 is a close-up right side back perspective view of the shoe of the embodiment of FIG. 1 without the orthotic.
Figure 9:
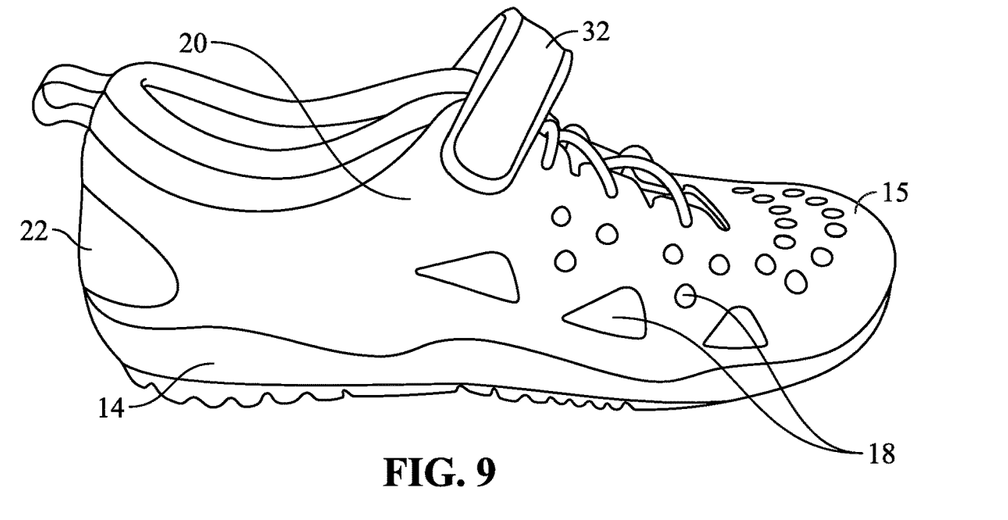
FIG. 9 is a close-up left side view of the shoe of the second embodiment of the shoe of the invention, without the orthotic shown, although the orthotic is like that shown in FIG. 1.
Figure 10:
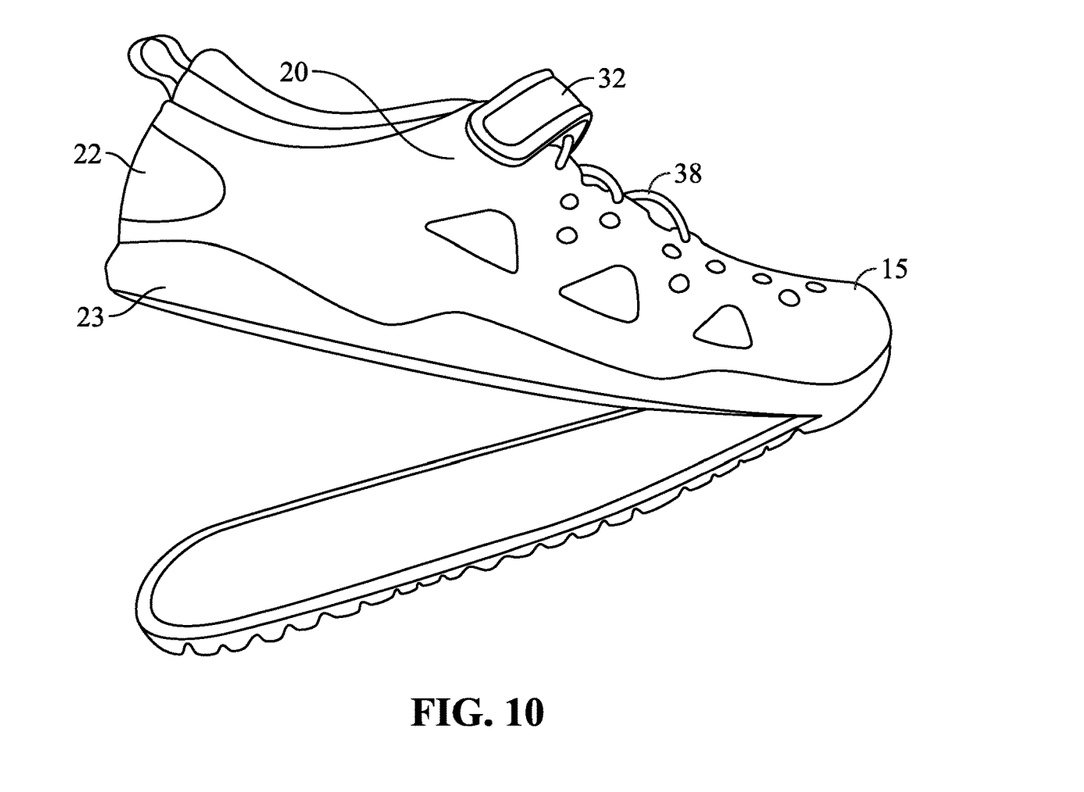
FIG. 10 is a close-up side view of the shoe of the embodiment of FIG. 9 showing the sole partially pulled away for insertion of the orthotic.

Similarly, pad 46 should be sufficiently strong as to receive the fastener(s) 51 for firmly holding the strap 45. Strap 45 can itself optionally have some padding comprised of material like that or similar to that comprising pad 50, and strap 45 is otherwise comprised of a silicone, soft plastic, rubber or synthetic polymeric or rubber type material, or an elastic type material, that is water resistant, or non-absorbent and quick drying, and substantially or effectively unchanged by water, and that is strong enough to hold the pad 45 which is holding the orthotic 12 to the wearer's leg during use in water. The configuration of the strap 45 attached to the pad 46 with buckle frame and bar 52 as shown in FIG. 5 (as opposed to direct attachment of the strap 45 to the pad 46 without the buckle frame and bar 52) affords more flexibility to the strap 45 for comfort to the wearer and allows for more adjustment of the strap 45.

After adjustment of strap 45 to fit the leg of the wearer, strap 45 is closed or fastened in place, for example, with a hook and loop closure such as "Velcro®," a registered trademark of Velcro Industries, B.V., or one or more buckles, ties, snaps, or similar fasteners.

The person's ankle will be supported, in the embodiments shown in the Figures with a support (not shown) in the ankle area 30, which preferably will have a pad or padding (not shown) between it and the person's ankle. As shown in FIGS. 1-3, 5-10, 16, and 17, strap 32 across the top 33 of the shoe near the ankle allows for adjustment in fit of the shoe. An additional strap 35 at the top 33 of the shoe near the top of the foot allows for further adjustment in fit as shown in FIGS. 1-3, and 5-8. Straps 32 and 35 in the embodiment shown in FIGS. 1-8 and strap 32 in the embodiment shown in FIGS. 9-16, are held closed with hook and loop fasteners such as "Velcro®," a registered trademark of Velcro Industries, B.V. However, other alternative fasteners could be used, such as for non-limiting example, laces or snaps, or elastic could be used in lieu of the straps. Straps 32 and 35 are comprised of the same material as the body of the shoe (which includes top 33 and sides 20), or the straps 32 and 35 can be comprised of material such as, for example, silicone, soft rubber or synthetic rube, for example, or soft plastic or similar polymer synthetic.

In the embodiments shown in the Figures, shoe 10 will have a front opening for receiving the foot into the shoe. In the embodiment shown in FIGS. 1-8, the straps 32 and 35 secure or effectuate closure of that opening. In the embodiment shown in FIGS. 9-16, laces 38 for tying secure or effectuate closure of the opening, and strap 32 allows for adjustment in fit while further securing closure of the opening of the shoe. In the embodiment shown in FIG. 17, the opening is secured with a zipper 44 and could alternatively be secured with an elastic pull, and strap 32 allows for adjustment in fit and further secures closure of the opening of the shoe.

The embodiment of the shoe 10 of the invention in FIG. 17 has an upper portion (above the ankle) or sleeve 39 comprised of neoprene or a similar material with similar properties of flexibility and water resistance as well as abrasion, impact and tear resistance. This sleeve 39 helps hold the orthotic 12 to the wearer's leg and the tightness or fit can be adjusted with strap 40. In the embodiment shown in FIG. 17, strap 40 is fastened or secured with a hook and loop fastener but other fasteners could be used, including laces or ties, snaps, or elastic, for example. The sleeve 39 can have padding. Preferably, the orthotic 12 will have a layer of padding (not shown) between it and the neoprene sleeve 39 against the wearer's skin. Such padding is comprised of material as described for pad 50, a foam type material or a shearling. Strap 40 is comprised of an elastic or a flexible, strong material such as silicone, soft rubber, or a synthetic rubber, for example, that is, a material that is non-absorbent or water resistant and quick drying, and not substantially or effectively changed by water.

In FIGS. 1-16, orthotic 12 has a curved section 16 which curves around the rear 22 of the shoe. FIG. 17 does not show the orthotic 12 but it is inserted in the shoe in the sole 14 as with the other embodiments shown and extends upward at the back of the shoe as with the other embodiments. However, in the embodiment of FIG. 17, the orthotic 12 can be positioned inside the rear 22 of the shoe and/or inside the sleeve 39 so that the sleeve 39 helps hold the orthotic in place against the leg of the wearer. The sleeve 39 can thereby cover all or part of the vertical portion 36 of the orthotic 12.

Preferably, the shoe 10 of the invention will be treated with an antimicrobial finish.

The water shoe of the invention is suitable for manufacture in a variety of sizes for use by children and adults. The amount of strength needed for the material comprising the orthotic and the amount of weight deemed tolerable for the orthotic depends on the size and strength of the wearer and the demands that wearer places on the orthotic, as would be readily understood and determinable by one of ordinary skill in the art.

It will be understood that other shoe configurations may be used to accomplish the principals and advantages of the present invention, and that other materials of construction than described, may be used for the shoe.

While preferred embodiments of the invention have been described, it should be understood that other various changes, adaptations and modifications can be made therein without departing from the spirit of the invention as reflected in the claims.

I claim:

1. A water or swim shoe for persons needing to wear an orthotic to support a foot for swimming or any other water exercise or recreation, the shoe comprising:
    an ankle and foot orthotic having a general "L" shape comprising an obtuse curved corner angle between a lower horizontal portion and an upper vertical portion, wherein the orthotic is comprised of a hard, rigid material not corroded by water, and sufficiently strong and light in weight to serve its purpose as an orthotic;
    a sole having toe and heel ends, two sides, and a base with a trench within for receiving the horizontal portion of the orthotic in the heel end;
    a shoe body connected to said toe and heel ends and said two sides of said sole, wherein said shoe body comprises:
        an opening in said shoe body for receiving said foot;
        two opposing side sections connecting to said sides of said sole;
        at least one first strap for adjusting the shoe on the foot or ankle;
        a least one hole in each side section sufficiently large for drainage of water;
    a toe section connected to said toe end of said sole, wherein said connected sole and toe section are capable of receiving said foot;
    a heel section connected to said heel end of said sole, comprising an ankle support with padding; and
    at least one pad and at least one second strap associated with the vertical portion of the orthotic for positioning between the back of the person's leg and the orthotic to hold that portion of the orthotic firmly in place on the leg;
    wherein the shoe body, the toe section, heel section, and the shoe sole are comprised of material or materials that are non-absorbent or water resistant and are not corroded by water.

2. The shoe of claim 1 wherein the shoe body is comprised of a water resistant, porous or mesh material.

3. The shoe of claim 1 wherein the shoe body is comprised of a water resistant, synthetic material from the group selected from plastics, vinyls, rubber, and synthetic rubber.

4. The shoe of claim 1 wherein said first strap is comprised of elastic or fastened with a hook and loop material.

5. The shoe of claim 1 wherein said second strap is comprised of elastic or fastened with a hook and loop material.

6. The shoe of claim 1 wherein the ankle support padding is comprised of a foam material.

7. The shoe of claim 1 wherein the pad associated with the orthotic is comprised of a foam material.

8. The shoe of claim 1 wherein the sole comprises at least one hole for water drainage.

9. The shoe of claim 1 wherein at least one of the two sides of the shoe body comprise a plurality of holes for water drainage.

10. The shoe of claim 1 wherein the toe end of the sole comprises rubber or a synthetic rubber that wraps over the top of the shoe body.

11. The shoe of claim 1 wherein the sole comprises rubber or synthetic rubber.

12. The shoe of claim 1 wherein the sole has an outer surface with a pattern for gripping and avoiding slippage.

13. The shoe of claim 1 wherein the orthotic is affixed to the sole with a waterproof sealant.

14. The shoe of claim 1 wherein the orthotic is comprised of a hard, rigid, plastic or similar synthetic polymeric material.

15. The shoe of claim 1 wherein the orthotic is comprised of stainless steel or an aluminum alloy not containing iron.

16. The shoe of claim 1 wherein said orthotic is one piece.

* * * * *